(12) United States Patent
Noguchi

(10) Patent No.: US 11,074,693 B2
(45) Date of Patent: Jul. 27, 2021

(54) ULTRASOUND DIAGNOSTIC APPARATUS AND METHOD OF PRODUCING ULTRASOUND IMAGE

(71) Applicant: FUJIFILM Corporation, Tokyo (JP)

(72) Inventor: Masafumi Noguchi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1401 days.

(21) Appl. No.: 14/166,260

(22) Filed: Jan. 28, 2014

(65) Prior Publication Data

US 2014/0213900 A1 Jul. 31, 2014

(30) Foreign Application Priority Data

Jan. 29, 2013 (JP) .............................. JP2013-014505

(51) Int. Cl.
*G06T 7/136* (2017.01)
*A61B 8/08* (2006.01)
(Continued)

(52) U.S. Cl.
CPC ................ *G06T 7/136* (2017.01); *A61B 8/00* (2013.01); *A61B 8/08* (2013.01); *A61B 8/085* (2013.01);
(Continued)

(58) Field of Classification Search
CPC ... A61B 8/5207; A61B 8/5269; A61B 8/0833; A61B 8/00; A61B 8/08; A61B 8/5215;
(Continued)

(56) References Cited

U.S. PATENT DOCUMENTS

| | | | | |
|---|---|---|---|---|
| 4,665,554 A | * | 5/1987 | Sternberg | ................. G06T 5/30 382/257 |
| 4,951,676 A | * | 8/1990 | Collet-Billon | ........ G01S 7/5206 600/437 |

(Continued)

FOREIGN PATENT DOCUMENTS

| | | | | |
|---|---|---|---|---|
| CN | 111311485 | * | 6/2020 | ............... G06T 7/12 |
| JP | 11-272865 A | | 10/1999 | |

(Continued)

*Primary Examiner* — Amanda Lauritzen Moher
(74) *Attorney, Agent, or Firm* — Birch, Stewart, Kolasch & Birch, LLP

(57) ABSTRACT

An ultrasound diagnostic apparatus, which transmits an ultrasonic wave toward a subject by an ultrasound probe, produces ultrasound image data based on obtained reception data by a diagnostic apparatus body, and displays an ultrasound image, includes a dilation processor which performs dilation processing on the ultrasound image data based on a dilation radius to produce dilated image data, an erosion processor which performs erosion processing on the ultrasound image data based on an erosion radius different in magnitude from the dilation radius to produce eroded image data, a difference processor which calculates difference between the dilated image data and the eroded image data to produce difference image data, and an edge enhancer which performs edge enhancement processing on the ultrasound image data based on the difference image data to produce edge enhanced image data.

11 Claims, 6 Drawing Sheets

(51) Int. Cl.
  *G06T 7/00* (2017.01)
  *A61B 8/00* (2006.01)
  *G06T 7/13* (2017.01)
  *G06T 7/12* (2017.01)
  *G06T 7/10* (2017.01)
  *G06T 7/254* (2017.01)
  *G06T 5/30* (2006.01)

(52) U.S. Cl.
  CPC .......... *A61B 8/0833* (2013.01); *A61B 8/0891* (2013.01); *A61B 8/5207* (2013.01); *A61B 8/5215* (2013.01); *A61B 8/5223* (2013.01); *A61B 8/5269* (2013.01); *G06T 5/30* (2013.01); *G06T 7/00* (2013.01); *G06T 7/0012* (2013.01); *G06T 7/10* (2017.01); *G06T 7/12* (2017.01); *G06T 7/13* (2017.01); *G06T 7/254* (2017.01); *A61B 8/52* (2013.01)

(58) Field of Classification Search
  CPC ..... A61B 8/085; A61B 8/5223; A61B 8/0891; G06T 7/254; G06T 7/00; G06T 7/10; G06T 7/136; G06T 7/12; G06T 7/13; G06T 7/0012; G06T 5/30
  See application file for complete search history.

(56) References Cited

U.S. PATENT DOCUMENTS

| | | | | |
|---|---|---|---|---|
| 5,583,346 A | * | 12/1996 | Nakajima | G06T 7/0012 250/587 |
| 5,714,764 A | * | 2/1998 | Takeo | G01N 23/043 250/587 |
| 5,787,208 A | * | 7/1998 | Oh | G06K 9/00127 382/128 |
| 6,047,090 A | * | 4/2000 | Makram-Ebeid | G06T 7/11 382/128 |
| 6,125,214 A | * | 9/2000 | Takeo | G06T 5/004 358/451 |
| 6,606,421 B1 | * | 8/2003 | Shaked | G06K 5/00 382/275 |
| 6,858,007 B1 | * | 2/2005 | Akselrod | A61B 6/466 128/916 |
| 6,993,203 B2 | * | 1/2006 | Ozawa | G06T 5/004 382/132 |
| 7,965,893 B2 | * | 6/2011 | Wu | G06T 7/12 382/199 |
| 2002/0076105 A1 | * | 6/2002 | Lee | G06T 7/155 382/190 |
| 2002/0181754 A1 | * | 12/2002 | Masumoto | G06T 7/0081 382/131 |
| 2003/0016868 A1 | * | 1/2003 | Oh | G06K 9/6202 382/190 |
| 2004/0042640 A1 | * | 3/2004 | Ikeda | G06T 5/005 382/115 |
| 2004/0151383 A1 | * | 8/2004 | Alessi | G06K 9/00 382/224 |
| 2004/0161160 A1 | * | 8/2004 | Recht | G06T 5/30 382/255 |
| 2004/0215076 A1 | * | 10/2004 | Kamiyama | G01S 7/52041 600/443 |
| 2005/0143655 A1 | * | 6/2005 | Satoh | G01S 7/52047 600/443 |
| 2005/0238248 A1 | * | 10/2005 | Mitsutani | G06T 5/30 382/257 |
| 2007/0286527 A1 | * | 12/2007 | Jabri | G06T 7/194 382/286 |
| 2008/0294049 A1 | * | 11/2008 | Guracar | G06T 7/248 600/458 |
| 2010/0054563 A1 | * | 3/2010 | Mendonca | A61B 6/032 382/131 |
| 2011/0125030 A1 | | 5/2011 | Bai et al. | |
| 2012/0269458 A1 | * | 10/2012 | Graziosi | G06T 3/403 382/299 |
| 2013/0271455 A1 | * | 10/2013 | Tsujita | A61B 8/5269 345/419 |
| 2014/0307941 A1 | * | 10/2014 | Zanella | G01M 17/027 382/141 |

FOREIGN PATENT DOCUMENTS

| | | | | |
|---|---|---|---|---|
| JP | 2000126178 | * | 5/2000 | ............. A61B 8/00 |
| JP | 2003-098117 A | | 4/2003 | |
| JP | 2007306489 | * | 11/2007 | ............. G06T 5/005 |
| JP | 2009512528 | * | 3/2009 | ............. G06T 1/00 |
| WO | WO 2009/128213 A1 | | 10/2009 | |

* cited by examiner

ULTRASOUND DIAGNOSTIC APPARATUS AND METHOD OF PRODUCING ULTRASOUND IMAGE

BACKGROUND OF THE INVENTION

The present invention relates to an ultrasound diagnostic apparatus and a method of producing an ultrasound image, and in particular, to an ultrasound diagnostic apparatus which produces an ultrasound image on the basis of a reception signal obtained by performing transmission and reception of an ultrasonic wave from an ultrasound probe, and displays the ultrasound image on a display unit.

An ultrasound diagnostic apparatus using an ultrasound image has hitherto been put into practical use in the field of medicine. In general, in this type of ultrasound diagnostic apparatus, an ultrasound image is produced by transmitting an ultrasonic beam from a transducer array of the ultrasound probe toward a subject, receiving an ultrasonic echo from the subject by the transducer array, and electrically processing a reception signal representing the reception of the ultrasonic echo in the diagnostic apparatus body.

In recent years, for example, as disclosed in WO 09/128213, JP 11-272865 A, and JP 2003-098117 A, an ultrasound diagnostic apparatus has been suggested, in which, when producing an ultrasound image, morphology processing, such as dilation processing and erosion processing, is used to perform image processing, such as noise removal or edge enhancement, on the ultrasound image, thereby improving image quality of the ultrasound image.

In edge enhancement processing, in a method using differentiation, a location in an image where the rate of change (gradient) is large is determined to be an edge. In contrast, in a method using dilation processing and erosion processing, a location in an image where change (amount of change, difference) is large is determined to be an edge, so that there is less influence of small granular noise, and thus it is possible to perform edge determination closer to human perception.

SUMMARY OF THE INVENTION

In ultrasound diagnosis, when it is desired to remove predetermined noise in an ultrasound image and to enhance an edge of a predetermined structure, it is possible to perform noise removal in the ultrasound image and edge enhancement of the structure using the dilation processing and erosion processing disclosed in WO 09/128213, JP 11-272865 A, and JP 2003-098117 A. However, the edge enhancement using the dilation processing and erosion processing may cause the occurrence of overshoot or undershoot due to over-enhancement. The overshoot refers to a phenomenon in which a rising portion of an edge protrudes upward, and the undershoot refers to a phenomenon in which a falling portion of an edge protrudes downward. The overshoot and undershoot chiefly occur in the case where enhancement is applied so as to restore an edge portion blurred due to smoothing for the purpose of noise removal.

When the edge enhancement is applied to the ultrasound image, in particular, the overshoot causes a problem. If overshoot occurs at the venous wall which should be thin originally, there exists the risk that a vein looks like an artery, or if overshoot occurs in a marginal region of the parenchyma of thyroid gland or the like, there exists the risk that the image is mistaken for a coarse image of the marginal region. For this reason, such occurrence of overshoot leads to a risk of an erroneous diagnosis in ultrasound diagnoses based on an ultrasound image.

In regard to the undershoot, although a falling portion of an edge of a region displayed in black, such as a blood vessel, is inconspicuous due to vignetting by a dynamic range, there is some possibility of causing an erroneous diagnosis similarly to the overshoot.

Accordingly, an object of the present invention is to provide an ultrasound diagnostic apparatus and a method of producing an ultrasound image which can suppress the occurrence of overshoot or undershoot in an ultrasound image at the time of edge enhancement processing of the ultrasound image.

In order to achieve such object, the present invention provides an ultrasound diagnostic apparatus which transmits an ultrasonic wave toward a subject by an ultrasound probe, produces ultrasound image data based on obtained reception data by a diagnostic apparatus body, and displays an ultrasound image, the ultrasound diagnostic apparatus comprising:

a dilation processor which performs dilation processing on the ultrasound image data based on a dilation radius to produce dilated image data;

an erosion processor which performs erosion processing on the ultrasound image data based on an erosion radius different in magnitude from the dilation radius to produce eroded image data;

a difference processor which calculates difference between the dilated image data and the eroded image data to produce difference image data; and an edge enhancer which performs edge enhancement processing on the ultrasound image data based on the difference image data to produce edge enhanced image data.

In the inventive ultrasound diagnostic apparatus as such, it is preferable that the dilation radius is greater than the erosion radius.

Preferably, the dilation radius is two or more times as great as the erosion radius.

More preferably, a ratio between the dilation radius and the erosion radius is 3:1 to 5:1.

The dilation radius may be smaller than the erosion radius.

It is also preferable that the ultrasound diagnostic apparatus further comprises:

a luminance value calculator which calculates a peripheral luminance value for each pixel of the ultrasound image; and a radius controller which controls each of the dilation radius for use in the dilation processing and the erosion radius for use in the erosion processing, wherein the radius controller controls each of the dilation radius and the erosion radius for each pixel based on the peripheral luminance value.

Preferably, the peripheral luminance value is an average value of luminance values of a plurality of peripheral pixels corresponding to one pixel of the ultrasound image.

It is preferable that the radius controller controls the dilation radius and the erosion radius so that the dilation radius becomes greater than the erosion radius when the peripheral luminance value calculated by the luminance value calculator is lower than a predetermined value, and so that the dilation radius becomes smaller than the erosion radius when the peripheral luminance value calculated by the luminance value calculator is higher than the predetermined value.

It is preferable that the radius controller controls the dilation radius and the erosion radius so that the dilation radius becomes greater than the erosion radius when the peripheral luminance value calculated by the luminance value calculator is lower than a predetermined value, and so that the dilation radius becomes smaller than the erosion radius when the peripheral luminance value calculated by the luminance value calculator is higher than the predetermined value.

The present invention also provides a method of producing an ultrasound image, in which an ultrasonic wave is transmitted toward a subject by an ultrasound probe, ultrasound image data is produced by a diagnostic apparatus body based on obtained reception data, and an ultrasound image is displayed, the method comprising the steps of:

performing dilation processing on the ultrasound image data based on a dilation radius to produce dilated image data, and performing erosion processing on the ultrasound image data based on an erosion radius different in magnitude from the dilation radius to produce eroded image data;

calculating difference between the dilated image data and the eroded image data to produce difference image data;

performing edge enhancement processing on the ultrasound image data based on the difference image data to produce edge enhanced image data; and displaying an ultrasound image based on the edge enhanced image data.

According to the invention, it is possible to provide an ultrasound image subjected to appropriate edge enhancement processing in which the occurrence of overshoot or undershoot in the ultrasound image is suppressed at the time of edge enhancement, and to prevent an erroneous diagnosis in ultrasound diagnoses.

DETAILED DESCRIPTION OF THE INVENTION

Hereinafter, embodiments of the invention will be described referring to the accompanying drawings.

Embodiment 1

Figure 1:
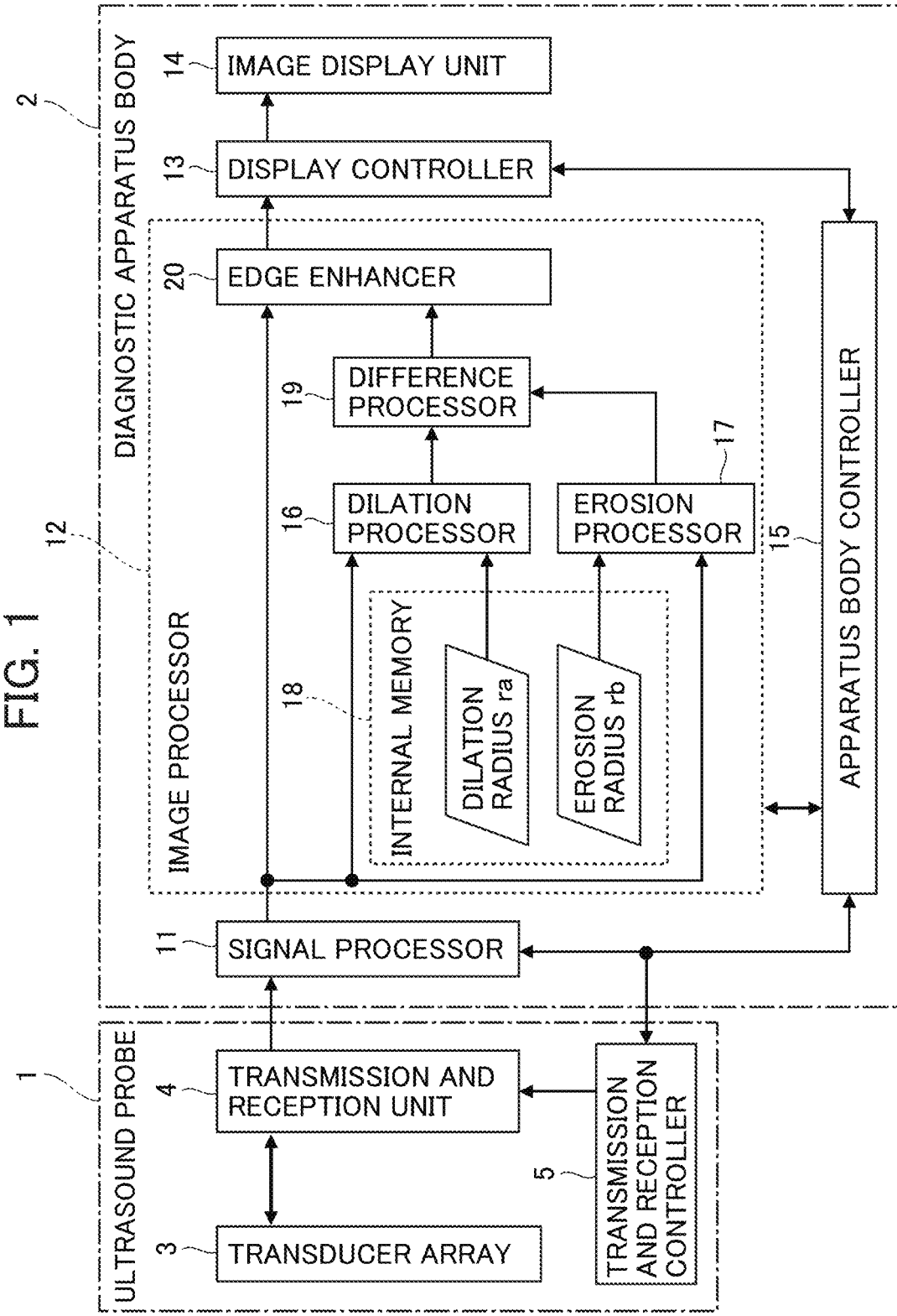
FIG. 1 is a block diagram showing the overall configuration of an ultrasound diagnostic apparatus according to Embodiment 1 of the invention.

FIG. 1 is a block diagram showing the overall configuration of an ultrasound diagnostic apparatus according to Embodiment 1. The ultrasound diagnostic apparatus includes an ultrasound probe 1 and a diagnostic apparatus body 2 connected to the ultrasound probe 1.

The ultrasound probe 1 includes a transducer array 3, a transmission and reception unit 4 is connected to the transducer array 3, and a transmission and reception controller 5 is connected to the transmission and reception unit 4.

In the diagnostic apparatus body 2, an image processor 12, a display controller 13, and an image display unit 14 are sequentially connected to a signal processor 11 which is connected to the transmission and reception unit 4 of the ultrasound probe 1, and an apparatus body controller 15 is connected to the signal processor 11, the image processor 12, and the display controller 13.

The transmission and reception controller 5 of the ultrasound probe 1 and the apparatus body controller 15 of the diagnostic apparatus body 2 are connected together.

The image processor 12 includes a dilation processor 16 connected to the signal processor 11, an erosion processor 17 also connected to the signal processor 11, an internal memory 18 which is connected to the dilation processor 16 and the erosion processor 17, and stores a dilation radius ra for use in the dilation processor 16 and an erosion radius rb for use in the erosion processor 17, a difference processor 19 connected to the dilation processor 16 and the erosion processor 17, and an edge enhancer 20 connected to the signal processor 11 and the difference processor 19.

The transducer array 3 of the ultrasound probe 1 has a plurality of ultrasound transducers arranged in a one-dimensional or two-dimensional manner. Each of the ultrasound transducers transmits an ultrasonic wave in accordance with a transmission signal supplied from the transmission and reception unit 4, receives an ultrasonic echo from a subject, and outputs a reception signal. Each ultrasound transducer is constituted by a vibrator in which electrodes are formed at both ends of a piezoelectric body composed of, for example, a piezoelectric ceramic represented by PZT (lead zirconate titanate), a piezoelectric polymer represented by PVDF (polyvinylidene difluoride), piezoelectric single crystal represented by PMN-PT (lead magnesium niobate-lead titanate solid solution), or the like.

If a pulsed or continuous-wave transmission signal voltage is applied across the electrodes of the vibrator, the piezoelectric body expands and contracts, whereby pulsed or continuous-wave ultrasonic waves are produced from the respective vibrators, and the ultrasonic waves are synthesized to form an ultrasonic beam. When receiving the propagating ultrasonic waves, the respective vibrators expand and contract to produce electric signals, and the electric signals are output as the reception signals of the ultrasonic waves.

The transmission and reception unit 4 adjusts the delay amount of each of the transmission signals on the basis of a transmission delay pattern selected in accordance with a control signal from the transmission and reception controller 5 so that the ultrasonic waves transmitted from the ultrasound transducers of the transducer array 3 form an ultrasonic beam, and supplies the transmission signals to the ultrasound transducers.

Further, the transmission and reception unit 4 amplifies and A/D converts the reception signal transmitted from each ultrasound transducer of the transducer array 3, and thereafter, performs reception focusing processing by giving a delay to each of the reception signals in accordance with a sound speed or the distribution of the sound speed set on the basis of a reception delay pattern selected in accordance with a control signal from the transmission and reception controller 5, and adding the reception signals. With this reception focusing processing, the focus of an ultrasonic echo is narrowed to produce reception data (sound ray signal).

The transmission and reception controller 5 controls the respective components of the ultrasound probe 1 on the basis of various control signals transmitted from the apparatus body controller 15 of the diagnostic apparatus body 2. Reception data produced in the transmission and reception unit 4 by an instruction of the transmission and reception controller 5 is sequentially output to the signal processor 11 of the diagnostic apparatus body 2.

The signal processor 11 of the diagnostic apparatus body 2 produces ultrasound image data on the basis of reception data, and outputs ultrasound image data to the dilation processor 16, the erosion processor 17, and the edge enhancer 20 of the image processor 12, respectively.

The image processor 12 performs predetermined image processing, such as noise removal, edge enhancement, or the like on ultrasound image data. Specific image processing is performed by the dilation processor 16, the erosion processor 17, the difference processor 19, and the edge enhancer 20 in the image processor 12.

The dilation processor 16 performs dilation processing on ultrasound image data output from the signal processor 11 on the basis of the dilation radius ra stored in advance in the internal memory 18 to produce dilated image data. The produced dilated image data is output to the difference processor 19.

Here, the dilation processing refers to processing in which, when referring to the values of all pixels within the range of the dilation radius ra centering on a predetermined pixel, the maximum value from among the pixels within the range of the dilation radius ra is set as the value of the center pixel.

The erosion processor 17 performs erosion processing on ultrasound image data output from the signal processor 11 on the basis of the erosion radius rb stored in advance in the internal memory 18 to produce eroded image data. The produced eroded image data is output to the difference processor 19.

Here, the erosion processing refers to processing in which, when referring to the values of all pixels within the range of the erosion radius rb centering on a predetermined pixel, the minimum value from among the pixels within the range of the erosion radius rb is set as the value of the center pixel.

The internal memory 18 stores the dilation radius ra for use in the dilation processing in the dilation processor 16 and the erosion radius rb for use in the erosion processing in the erosion processor 17, and outputs these pieces of information to the dilation processor 16 and the erosion processor 17 as necessary. For example, the dilation radius ra and the erosion radius rb are input from an operation input unit (not shown) by an operator and stored in the internal memory 18 through the apparatus body controller 15.

In the conventional edge processing, the dilation radius ra and the erosion radius rb have the same value, whereas, in the edge processing according to the invention, the dilation radius ra and the erosion radius rb have different values. That is, in regard to the dilation radius ra and the erosion radius rb, different values are input. Specifically, the dilation radius ra is set to be greater than the erosion radius rb (ra>rb), whereby it is possible to suppress the occurrence of overshoot in the ultrasound image. Furthermore, the erosion radius rb is set to be greater than the dilation radius ra (rb>ra), whereby it is possible to suppress the occurrence of undershoot in the ultrasound image.

The difference processor 19 calculates the difference between dilated image data output from the dilation processor 16 and eroded image data output from the erosion processor 17 to produce difference image data. The produced difference image data is output to the edge enhancer 20.

The edge enhancer 20 performs edge enhancement processing on the ultrasound image on the basis of ultrasound image data output from the signal processor 11 and difference image data output from the difference processor 19. Specifically, ultrasound image data is multiplied by difference image data to produce edge enhanced image data in which the edge of the ultrasound image is enhanced. The produced edge enhanced image data is output to the display controller 13.

The display controller 13 converts edge enhanced image data output from the edge enhancer 20 of the image processor 12 into display image data displayable on the image display unit 14, and causes the image display unit 14 to display the ultrasound image subjected to the edge enhancement processing on the basis of an instruction of the apparatus body controller 15.

The image display unit 14 includes, for example, a display device, such as an LCD, and displays the ultrasound image under the control of the display controller 13.

The apparatus body controller 15 controls the respective components in the diagnostic apparatus body 2 by an operation instruction input from the operation input unit (not shown) by the operator.

While the signal processor 11, the image processor 12, and the display controller 13 are constituted by a CPU and operation programs which cause the CPU to perform various kinds of processing, these may be constituted by digital circuits.

Next, the operation of the ultrasound diagnostic apparatus according to Embodiment 1 of the invention will be described.

An operator brings the ultrasound probe 1 into contact with skin near a site to be examined (for example, the liver) of the subject and starts ultrasound diagnosis.

Ultrasonic beams are sequentially transmitted from the ultrasound transducers of the transducer array 3 to the inside of the subject on the basis of the driving signals from the transmission and reception unit 4 of the ultrasound probe 1, and reception signals representing the reception of ultrasonic echoes from the subject by the ultrasound transducers are sequentially output to the transmission and reception unit 4, whereby reception data is produced. Reception data is sequentially output to the signal processor 11 of the diagnostic apparatus body 2.

The signal processor 11 produces ultrasound image data on the basis of reception data, and outputs ultrasound image data to the dilation processor 16, the erosion processor 17, and the edge enhancer 20 of the image processor 12.

In the dilation processor 16, dilation processing is performed on ultrasound image data on the basis of the dilation radius ra stored in advance in the internal memory 18 to produce dilated image data. In the erosion processor 17, erosion processing is performed on ultrasound image data on the basis of the erosion radius rb stored in advance in the internal memory 18 to produce eroded image data. The dilation radius ra and the erosion radius rb stored in advance in the internal memory 18 are set to different values. Dilated image data produced by the dilation processor 16 and eroded image data produced by the erosion processor 17 are output to the difference processor 19.

The difference processor 19 produces difference image data on the basis of dilated image data produced by the dilation processor 16 and eroded image data produced by the erosion processor 17. The difference processor 19 outputs difference image data to the edge enhancer 20.

The edge enhancer 20 produces edge enhanced image data on the basis of ultrasound image data output from the signal processor 11 and difference image data output from the difference processor 19. Specifically, ultrasound image data is multiplied by difference image data to produce edge enhanced image data.

Edge enhanced image data is output to the display controller 13, is converted into display image data displayable on the image display unit 14, and is displayed on the image display unit 14 by an instruction of the apparatus body controller 15. An ultrasound image subjected to appropriate edge enhancement processing is displayed on the image display unit 14 by the display controller 13 through the apparatus body controller 15.

Next, the enhanced ultrasound image subjected to the conventional edge enhancement processing in which the dilation radius ra and the erosion radius rb have the same value is compared with the enhanced ultrasound image subjected to edge enhancement processing according to an example of the invention in which the dilation radius ra and the erosion radius rb have different values. In the conventional edge enhancement processing, both the dilation radius ra and the erosion radius rb are three pixels, and in the inventive edge enhancement processing, the dilation radius ra is five pixels and the erosion radius rb is one pixel.

Figure 2:
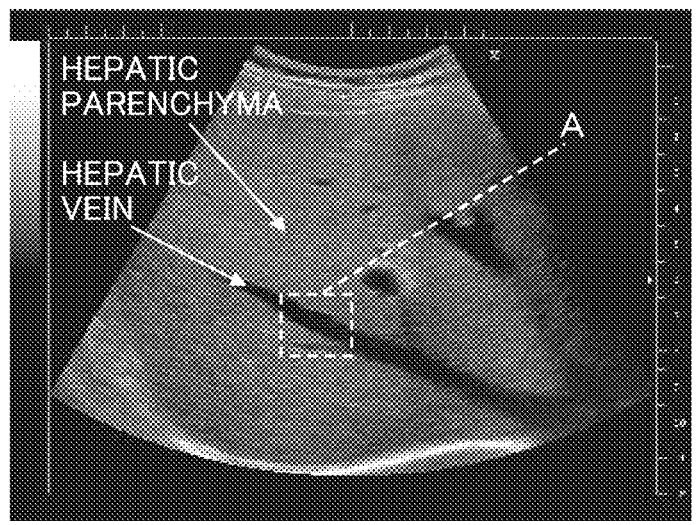
FIG. 2 shows an example of an ultrasound image when a liver is imaged in the ultrasound diagnostic apparatus according to the invention.

FIG. 2 shows an ultrasound image of a liver based on ultrasound image data produced by the signal processor 11. As shown in FIG. 2, a hepatic vein extending in black can be recognized in the hepatic parenchyma.

Figure 3:
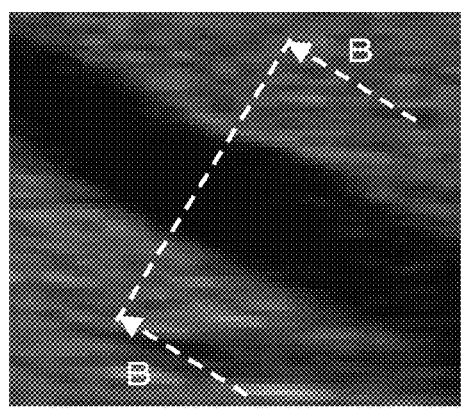
FIG. 3 shows an ultrasound image obtained by extracting a hepatic vein portion surrounded by the dotted line A in the ultrasound image shown in FIG. 2.

FIG. 3 is an enlarged view of a hepatic vein portion surrounded by the dotted line A in FIG. 2. The conventional edge enhancement processing and the edge enhancement processing according to the invention are compared with each other on the basis of the profile along the dotted line B-B shown in FIG. 3.

Figure 4:
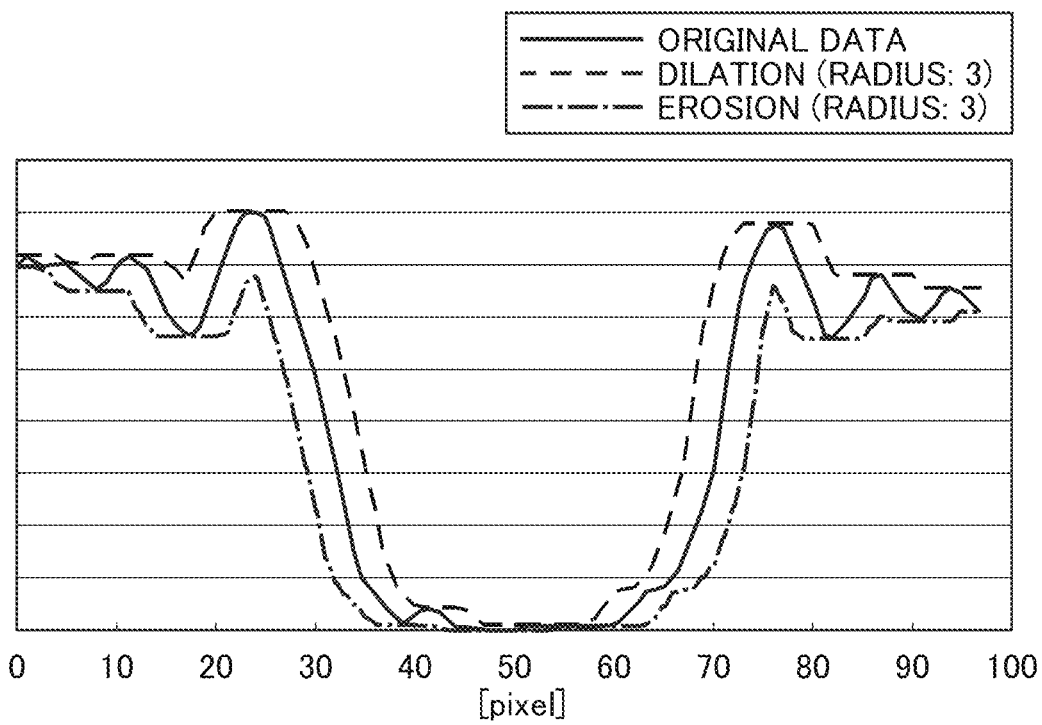
FIG. 4 is a graph showing the profile along the dotted line B-B in the ultrasound image shown in FIG. 3, and the profiles along the dotted line B-B obtained when dilation processing is performed with dilation radius ra of three pixels and when erosion processing is performed with erosion radius rb of three pixels, respectively.

FIG. 4 is a graph showing the profile along the dotted line B-B in the ultrasound image shown in FIG. 3, and the profiles along the dotted line B-B in a dilated image and an eroded image obtained when dilation processing and erosion processing are performed with the dilation radius ra and the erosion radius rb having the same value of three pixels in the conventional edge enhancement processing. In the graphs of FIGS. 4 to 7, the vertical axis represents the value of luminance, and the horizontal axis represents the number of pixels which corresponds to the distance.

Figure 5:
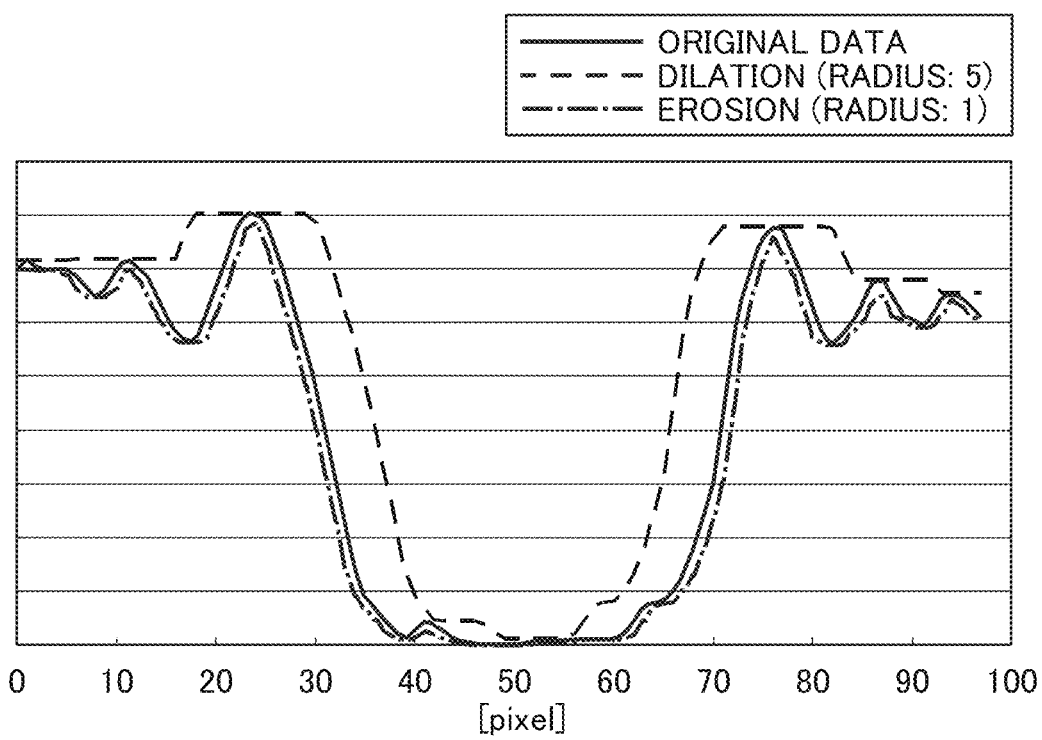
FIG. 5 is a graph showing the profile along the dotted line B-B in the ultrasound image shown in FIG. 3, and the profiles along the dotted line B-B obtained when dilation processing is performed with dilation radius ra of five pixels and when erosion processing is performed with erosion radius rb of one pixel, respectively.

In contrast, FIG. 5 is a graph showing the profile along the dotted line B-B in the ultrasound image shown in FIG. 3, and the profiles along the dotted line B-B in a dilated image and an eroded image when dilation processing and erosion processing are performed with the dilation radius ra and the erosion radius rb having different values, that is, with the dilation radius ra of five pixels and the erosion radius rb of one pixel, in the edge enhancement processing according to the invention.

In the conventional edge enhancement processing, when the dilation radius ra and the erosion radius rb have the same value of three pixels, as shown in the graph of FIG. 4, it is understood that dilation processing and erosion processing are equally performed on the original data. In contrast, in the edge enhancement processing according to the invention, when dilation processing and erosion processing are performed with the dilation radius ra of five pixels and the erosion radius rb of one pixel, as shown in the graph of FIG. 5, it is understood that, while the original data is largely changed by the dilation processing, the original date is hardly changed by the erosion processing.

Figure 6:
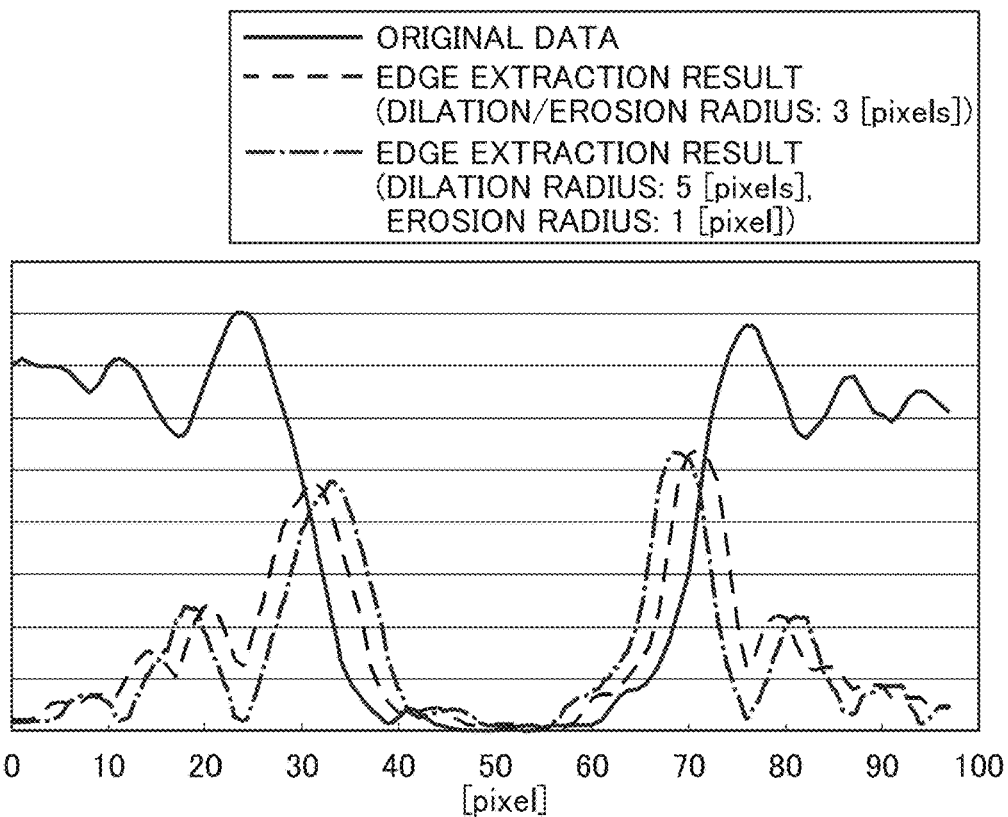
FIG. 6 is a graph showing the profile along the dotted line B-B in the ultrasound image shown in FIG. 3, the difference between the profile when dilation processing shown in FIG. 4 is performed and the profile when erosion processing shown in FIG. 4 is performed, and the difference between the profile when dilation processing shown in FIG. 5 is performed and the profile when erosion processing shown in FIG. 5 is performed.

FIG. 6 is a graph showing the profile along the dotted line B-B shown in FIG. 3 (the original data), the profile corresponding to difference image data when the dilation radius ra and the erosion radius rb have the same value of three pixels in the conventional edge processing, and the profile corresponding to difference image data when the dilation radius ra and the erosion radius rb have different values, that is, the dilation radius ra has a value of five pixels and the erosion radius rb has a value of one pixel, in the edge processing according to the invention. In the difference image data with the dilation radius ra of five pixels and the erosion radius rb of one pixel, each peak of luminance value is located nearer to the center of the hepatic vein than each peak of luminance value in the difference image data with the dilation radius ra and the erosion radius rb of three pixels each. That is, it is understood that difference image data according to the invention is extracted in a state where it comes close to the falling side of the edge.

Figure 7:
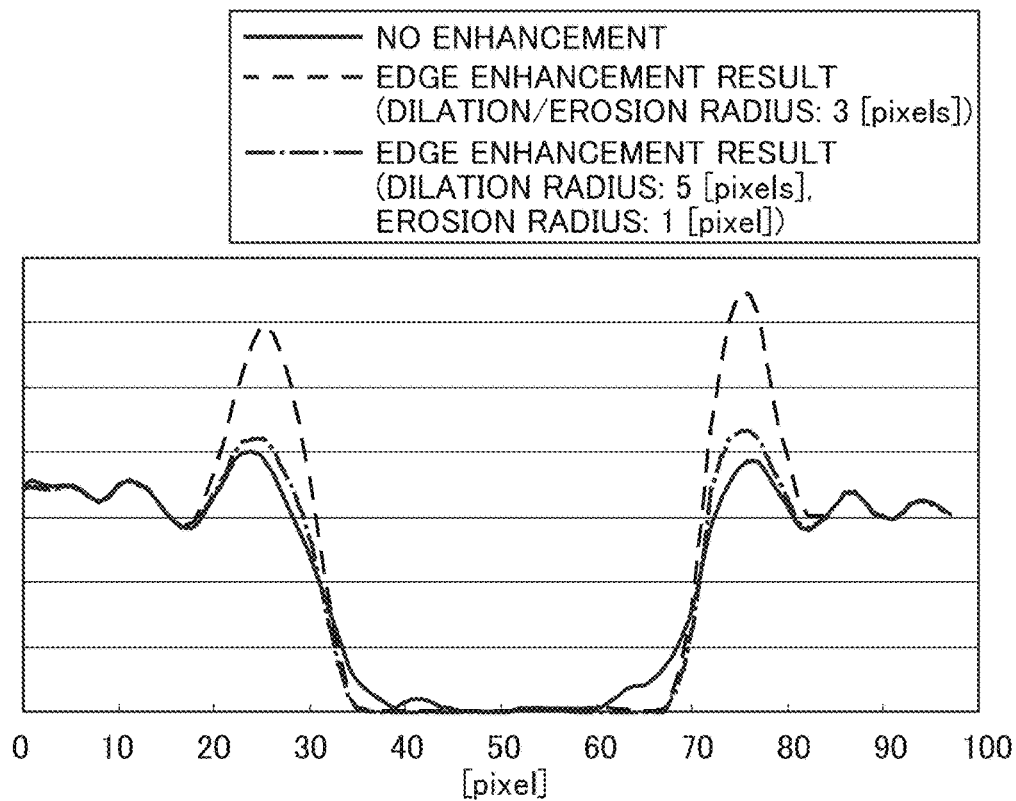
FIG. 7 is a graph showing the profile along the dotted line B-B in the ultrasound image shown in FIG. 3, and the respective profiles along the dotted line B-B obtained when edge enhancement processing is performed on the ultrasound image on the basis of the conventional difference image data and when edge enhancement processing is performed on the ultrasound image on the basis of the difference image data according to the invention.

FIG. 7 is a graph showing the profile along the dotted line B-B shown in FIG. 3 (the original data), the profile corresponding to edge enhanced image data subjected to edge enhancement processing with the dilation radius ra and the erosion radius rb having the same value of three pixels in the conventional edge processing, and the profile corresponding to edge enhanced image data subjected to edge enhancement processing with the dilation radius ra and the erosion radius rb having different values, that is, with the dilation radius ra of five pixels and the erosion radius rb of one pixel in the edge processing according to the invention.

Figure 8A:
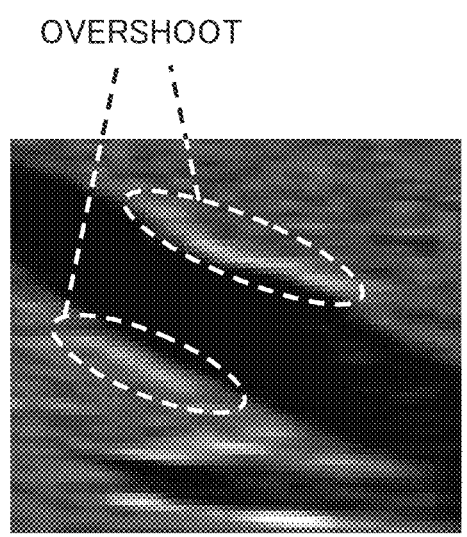
FIG. 8A shows an enhanced ultrasound image obtained by performing the conventional edge enhancement processing on the ultrasound image shown in FIG. 3.
Figure 8B:
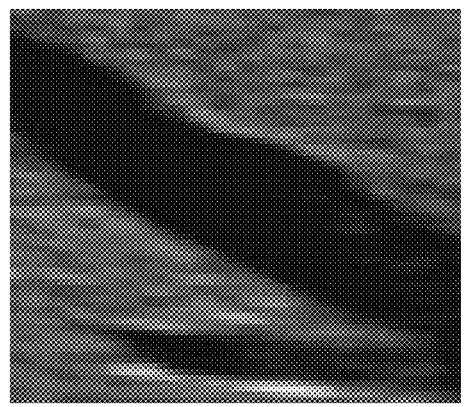
FIG. 8B shows an enhanced ultrasound image obtained by performing the edge enhancement processing according to the invention on the ultrasound image shown in FIG. 3.

Correspondingly to the ultrasound image of FIG. 3, FIG. 8A shows an enhanced ultrasound image subjected to edge enhancement processing with the dilation radius ra and the erosion radius rb having the same value of three pixels in the conventional edge processing, and FIG. 8B shows an enhanced ultrasound image subjected to edge enhancement processing with the dilation radius ra and the erosion radius rb having different values, that is, with the dilation radius ra of five pixels and the erosion radius rb of one pixel in the edge processing according to the invention.

In FIG. 8A, as will be understood from the portions surrounded by the dotted lines, overshoot occurs near the hepatic vein which is displayed in black, and whitens the image. With confirmation being found in the graph of FIG. 7 corresponding to FIG. 8A, it is understood that steep enhancement which is considered to be overshoot occurs in front of and behind the hepatic vein.

Accordingly, when the operator or the physician performs diagnosis on the basis of the ultrasound image of FIG. 8A which is subjected to the edge enhancement processing, there is some possibility of erroneously determining the hepatic vein as a hepatic artery having a thick blood vessel wall due to the overshoot which is observed in the image as white parts.

In contrast, in FIG. 8B, overshoot does not occur near the black hepatic vein, and when confirmation is found in the corresponding graph of FIG. 7, it is understood that an appropriate edge enhancement is performed compared to the graph of the conventional edge enhancement, and the boundary between the hepatic vein and the hepatic parenchyma is drawn sharply without causing overshoot.

In FIGS. 8A and 8B, while undershoot should primarily occur in the falling portion of the edge, the undershoot does not appear in a profile due to vignetting by a dynamic range during the display of the images.

As will be apparent from the above, in the ultrasound diagnostic apparatus according to Embodiment 1, a difference is provided in advance between the dilation radius ra and the erosion radius rb, and in particular, the dilation radius ra is set to be greater than the erosion radius rb, whereby it is possible to suppress the occurrence of overshoot in an ultrasound image at the time of edge enhancement processing and thus it is possible for an operator or a physician to perform an appropriate diagnosis on the basis of the ultrasound image without concerning about an erroneous diagnosis due to overshoot. Similarly, the erosion radius rb is set to be greater than the dilation radius ra, whereby it is possible to suppress the occurrence of undershoot in an ultrasound image.

Embodiment 2

In the ultrasound diagnostic apparatus according to Embodiment 1, the dilation radius ra and the erosion radius rb are set and stored in advance in the internal memory 18, and uniform dilation processing and uniform erosion processing are performed on ultrasound image data on the basis of the dilation radius ra and the erosion radius rb.

In contrast, the dilation radius ra and the erosion radius rb may also be controlled for each region of an ultrasound image, thereby performing more suitable edge enhancement.

Figure 9:
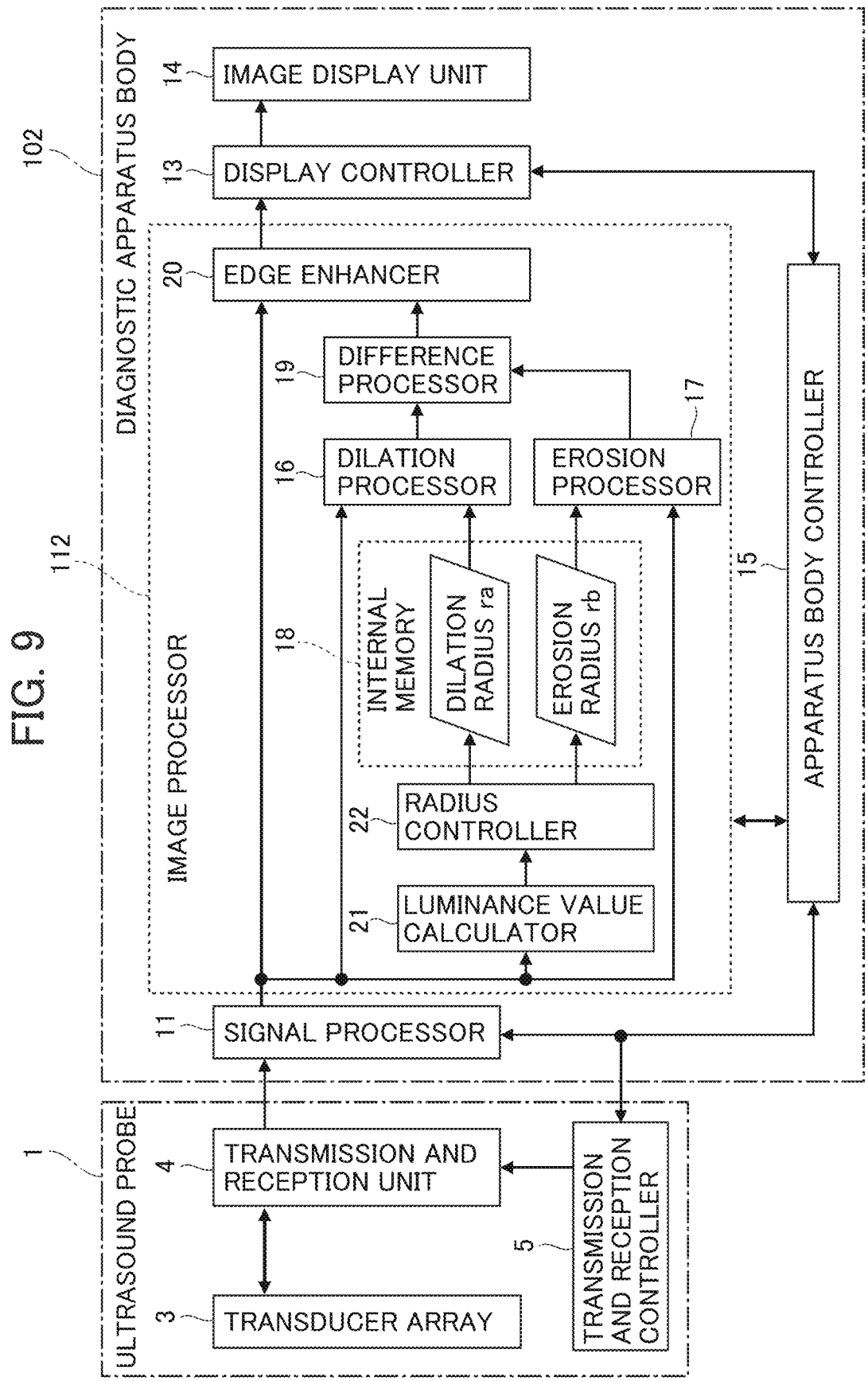
FIG. 9 is a block diagram showing the overall configuration of an ultrasound diagnostic apparatus according to Embodiment 2 of the invention.

In an ultrasound diagnostic apparatus according to Embodiment 2, for example, a luminance value calculator 21 and a radius controller 22 are added to the image processor 12 of the diagnostic apparatus body 2 shown in FIG. 1 so as to configure an image processor 112 of a diagnostic apparatus body 102 shown in FIG. 9. The ultrasound diagnostic apparatus according to Embodiment 2 has the same configuration as the ultrasound diagnostic apparatus according to Embodiment 1 except that the luminance value calculator 21 and the radius controller 22 are added.

The signal processor 11 is connected to the dilation processor 16, the erosion processor 17, and the edge enhancer 20 of the image processor 112, and is also connected to the luminance value calculator 21 thereof.

The luminance value calculator 21 is connected to the radius controller 22, the radius controller 22 is connected to the internal memory 18, and the internal memory 18 is connected to the dilation processor 16 and the erosion processor 17.

The luminance value calculator 21 of the image processor 112 calculates an average value of luminance values of a plurality of peripheral pixels with respect to a predetermined pixel as a peripheral luminance value on the basis of ultrasound image data. Information regarding the calculated peripheral luminance value for each pixel is output to the radius controller 22.

The radius controller 22 determines the dilation radius ra and the erosion radius rb for each pixel from information regarding the peripheral luminance value for each pixel. Specifically, the dilation radius ra in the dilation processor 16 and the erosion radius rb in the erosion processor 17 are controlled so that the erosion radius rb is set to be greater than the dilation radius ra (rb>ra) when the peripheral luminance value is higher than a predetermined value and the dilation radius ra is set to be greater than the erosion radius rb (ra>rb) when the peripheral luminance value is lower than the predetermined value. Information regarding the dilation radius ra and the erosion radius rb for each pixel determined by the radius controller 22 is stored in the internal memory 18.

The dilation processor 16 performs dilation processing on the basis of the dilation radius ra which is determined by the radius controller 22 and stored in the internal memory 18, and the erosion processor 17 performs erosion processing on the basis of the erosion radius rb which is determined by the radius controller 22 and stored in the internal memory 18.

The ultrasound diagnostic apparatus according to Embodiment 2, exclusive of the luminance value calculator 21 and the radius controller 22, is identical in configuration and operation to the apparatus of Embodiment 1.

In the ultrasound diagnostic apparatus according to Embodiment 2 of the invention, by using information regarding a luminance value of an ultrasound image, the radii are controlled so that the occurrence of overshoot is suppressed in the periphery of a region having a comparatively low luminance value (a region displayed in black, such as a blood vessel), and to the contrary, the radii are controlled so that the occurrence of undershoot is suppressed in the periphery of a region having a comparatively high luminance value (a region of calcification, bone, or the like). Therefore, it is possible to apply more appropriate enhancement processing to an ultrasound image and to display an ultrasound image subjected to more appropriate enhancement processing.

In the invention, the ratio between the dilation radius ra and the erosion radius rb depends on whether overshoot or undershoot is to be suppressed to what extent, the type of the subject (liver or the like), and so forth. In a portion displayed in black, such as a blood vessel in an ultrasound image, as one guideline for the suppression of overshoot, it is preferable that the dilation radius ra is set to be two or more times as great as the erosion radius rb. A ratio between the dilation radius ra and the erosion radius rb of about 3:1 to 5:1 is particularly preferred.

Appropriate values of the dilation radius ra and the erosion radius rb vary with the resolution of an input image, the type of the subject, imaging conditions (the frequency band or the center frequency of the ultrasound probe 1), the frequency or bandwidth of an ultrasonic wave to be transmitted, the scan line density, filter characteristics of detection processing at the time of reception, imaging methods such as harmonic imaging, and the like. With respect to the order, several pixels are suitable for a normal ultrasound image.

While the ultrasound diagnostic apparatus according to Embodiments 1 and 2 of the present invention have been described above in detail, the present invention is not limited thereto and may be improved or modified in various forms without departing from the gist of the invention.

What is claimed is:

1. An ultrasound diagnostic apparatus which transmits an ultrasonic wave toward a subject by an ultrasound probe, produces ultrasound image data based on obtained reception data by a diagnostic apparatus body, the ultrasound diagnostic apparatus comprising:
    a dilation processor which performs dilation processing on acquired ultrasound image data based on a dilation radius to produce dilated image data;
    an erosion processor which performs erosion processing on the acquired same ultrasound image data that the dilation processing is performed on based on an erosion radius different in magnitude from the dilation radius to produce eroded image data;
    a difference processor which calculates difference between the dilated image data and the eroded image data to produce difference image data; and
    a computer processor,
    wherein the dilated image data, the eroded image data and the difference image data are values of peripheral average luminance for each pixel of an ultrasound image based on the acquired ultrasound image data; and
    wherein the computer processor performs edge enhancement processing on the ultrasound image data by multiplying the acquired ultrasound image data with the difference image data to produce edge enhanced image data.

2. The ultrasound diagnostic apparatus according to claim 1,
    wherein the dilation radius is greater than the erosion radius.

3. The ultrasound diagnostic apparatus according to claim 1,
    wherein the dilation radius is two or more times as great as the erosion radius.

4. The ultrasound diagnostic apparatus according to claim 1,
    wherein a ratio between the dilation radius and the erosion radius is 3:1 to 5:1.

5. The ultrasound diagnostic apparatus according to claim 1,
    wherein the dilation radius is smaller than the erosion radius.

6. The ultrasound diagnostic apparatus according to claim 1,
    wherein the computer processor
    controls each of the dilation radius for use in the dilation processing and the erosion radius for use in the erosion processing, and
    controls each of the dilation radius and the erosion radius for each pixel based on the peripheral luminance value.

7. The ultrasound diagnostic apparatus according to claim 6,
    wherein the computer processor controls the dilation radius and the erosion radius so that the dilation radius becomes greater than the erosion radius when the peripheral luminance value calculated by the computer processor is lower than a predetermined value, and so that the dilation radius becomes smaller than the erosion radius when the peripheral luminance value calculated by the computer processor is higher than the predetermined value.

8. The ultrasound diagnostic apparatus according to claim 6,
    wherein the computer processor controls the dilation radius and the erosion radius so that the dilation radius becomes greater than the erosion radius when the peripheral luminance value calculated by the computer processor is lower than a predetermined value, and so that the dilation radius becomes smaller than the erosion radius when the peripheral luminance value calculated by the computer processor is higher than the predetermined value.

9. The ultrasound diagnostic apparatus according to claim 1,
    wherein the computer processor further produces an ultrasound image based on the edge enhanced image data, and
    wherein the ultrasound diagnostic apparatus further comprises a monitor that displays the ultrasound image.

10. The ultrasound diagnostic apparatus according to claim 1,
    wherein the computer processor controls each of the dilation radius and the erosion radius for each pixel based on the peripheral luminance value for each pixel.

11. A method of producing an ultrasound image, in which an ultrasonic wave is transmitted toward a subject by an ultrasound probe, ultrasound image data is produced by a diagnostic apparatus body based on obtained reception data, the method comprising the steps of:
    performing dilation processing on acquired ultrasound image data based on a dilation radius to produce dilated image data, and performing erosion processing on the acquired same ultrasound image data that the dilation processing is performed on based on an erosion radius different in magnitude from the dilation radius to produce eroded image data;
    calculating difference between the dilated image data and the eroded image data to produce difference image data;
    performing edge enhancement processing on the ultrasound image data by multiplying the acquired ultrasound image data with the difference image data to produce edge enhanced image data; and
    displaying an ultrasound image based on the edge enhanced image data,
    wherein the dilated image data, the eroded image data and the difference image data are values of peripheral average luminance for each pixel of an ultrasound image based on the acquired ultrasound image data.

* * * * *